United States Patent

Prussia et al.

[11] Patent Number: 5,372,030
[45] Date of Patent: Dec. 13, 1994

[54] NON-DESTRUCTIVE FIRMNESS MEASURING DEVICE

[75] Inventors: Stanley E. Prussia, Griffin; John J. Astleford, Stone Mountain; Bob Hewlett, Lilburn; Yen-Con Hung, Peachtree City, all of Ga.

[73] Assignee: The University of Georgia Research Foundation, Inc., Athens, Ga.

[21] Appl. No.: 120,956

[22] Filed: Sep. 15, 1993

[51] Int. Cl.$^5$ ............... G01B 11/02; G01N 3/10
[52] U.S. Cl. .................. 73/37; 209/509; 356/355; 356/356; 356/3; 356/446; 73/37.5; 73/81; 73/37.8
[58] Field of Search ......... 356/355, 356, 3, 446, 356/385; 209/509; 73/37.5, 37, 81, 37.8

[56] References Cited

U.S. PATENT DOCUMENTS

| | | | |
|---|---|---|---|
| 3,181,351 | 5/1965 | Stauffer | 73/80 |
| 3,232,099 | 2/1966 | Motchenbacher | 73/80 |
| 3,246,507 | 4/1966 | Hyde | 73/37.5 |
| 3,304,769 | 2/1967 | Stauffer | 73/80 |
| 3,668,928 | 6/1972 | Strydom | 73/37.5 |
| 3,694,800 | 9/1972 | Frank | 73/37.5 |
| 3,785,201 | 1/1974 | Rubio et al. | 73/81 |
| 4,061,020 | 12/1977 | Fridley et al. | 73/81 |
| 4,088,009 | 5/1978 | Futruda | 73/37.8 |
| 4,798,469 | 1/1989 | Burke | 356/385 |
| 4,884,696 | 12/1989 | Peleg | 73/579 |
| 4,986,111 | 1/1991 | Sidley | 73/37.5 |
| 5,235,406 | 8/1993 | Ishii et al. | 356/356 |
| 5,267,016 | 11/1993 | Meinzer et al. | 356/3 |

OTHER PUBLICATIONS

"Laser Displacement Sensors Lb–1000 Series", *Keyence Corporation*, Cat. No. LB3 (1992).
"Keystone General Catalog", pp. 2–9, 2.1–2.10, 3.1–3.5 (undated).
"General Catalog–Measuring Instruments", *Keyence Corporation*, No. KA–ME–04 (1st Ed. 1991).
"Laser Analog Displacement Sensor" LAS–5010–/LAS–8010), *Adsens Tech, Inc.*
"Measuring Applications", *Keyence Corp. of America.*
"Laser Displacement Sensor Instruction Manual" (LB–11), *Keyence Corporation*, pp. 9–10.
"Sensing Fruit & Vegetable Firmness", *Bard '93*, pp. 1–23.
Magness and Taylor, "An Improved Type of Pressure Tester For The Determination Of Fruit Maturity", *U.S. Dept. Agric.*, Cir. 350:1–8 (Sep. 1925).
Peleg, K., "Comparison of Non–destructive and Destructive Measurement of Apple Firmness", *J. Agric. Engng. Res.*, 55:227–238 (1993).
Nahir et al., "Tomato Grading By Impact Force Response", *ASAE*, Paper No. 86–3028:1–12 (1986).
"Measuring Of Produce Softening", *Meded, Landbouwhogeschool Wageningen*, 68–15:34–69 (1968).
Lichtensteiger et al., "Impact Parameters of Spherical Viscoelastic Objects and Tomatoes", *Transactions of the ASAE*, 31(2):595–602 (Mar./Apr. 1988).
Pitts et al., "Evaluation of the PFT Apple Firmness Sensor", *ASAE*, Paper No. 91–3017:1–17 (1991).
Delwiche et al., "A Second Generation Fruit Firmness Sorter", *ASAE*, Paper No. 91–6042:1–10 with FIGS. 1–6 (1991).
Delwiche et al., "Technology and Principles for Assessing and Retaining Quality of Fruits and Vegetables", *Dep. of Agric. Engng.*, Un. of Calif., Davis, NE–179, 6 pp. unnumbered (no date).
Delwiche and Bowers, "Signal Processing of Fruit Impact Forces For Firmness Detection", *ASAE*,Paper No. 85–3029:1–20 (1985).
Chen et al., "Instrument For Testing The Response of Fruits To Impact", *ASAE*, Paper No. 85–3537:1–12 (1985).
"Compression Test Of Food Materials Of Convex Shape", *ASAE Standard*, S368.2:5 pp. unnumbered (Rev. Mar./1990).
McDonald and Delwiche, "Non–Destructive Sensing Of Peach Flesh Firmness Using Impact Force Analysis", *ASAE*, 83–6540:1–11 with FIGS. 1–2 (1983).
Mizrach et al., "Non–Destructive Impact Tests Of Fruit", *ASAE*, Paper No. 906042:1–13 (1990).
Delwiche and Sarig, "A Probe Impact Sensor For Fruit Texture Measurement", *ASAE*, Paper No. 89–6609:1–22 (1989).
Abbott et al., "Effe–gi, Magness–Taylor, and Instrom Fruit Pressure Testing Devices for Apples, Peaches, and Nectarines", *J. Amer. Soc. Hort. Sci.* 101(6):698–700 (1976).

Armstrong et al., "Progress On An Acoustic Technique For Estimating Apple Firmness", *ASAE*, Paper No. 92-6050:1–14 (1992).

Bryan et al., "Mechanically Assisted Grading of Oranges for Processing", *Transactions of the ASAE*, 1226–1231 (1978).

Chen and Sun, "A Review of Non-destructive Methods for Quality Evaluation and Sorting of Agricultural Products", *J. Agric. Engng Res.* 49:85–98 (1991).

Dawson, G. A., "Non-Destructive Firmness Testing of Kiwifruit", *DSIR Indus. Dev.*, 79 (no date).

Delwiche et al., "Determination of Peach Firmness by Analysis of Impact Forces", *ASAE*, vol. 30(1):249–254 (1987).

Lichtenstgeiger et al., "Impact Parameters of Spherical Viscoelastic Objects and Tomatoes", *Transactions of ASAE*, vol. 32(2):595–602 (1988).

Meredith et al., "Detection of Firmness in Peaches by Impact Force Response", *Transactions of ASAE*, vol. 33(1):186–188 (1990).

Mehlschau et al., "A Deformeter for Non-Destructive Maturity Detection of Pears", *Transactions of ASAE*, 1368–1371, 1375 (1981).

Mizrach et al., "Mechanical Thumb Sensor For Fruit And Vegetable Sorting", *Transactions of ASAE*. vol. 35(1):247–250 (1992).

Perry, J. S., "A Nondestructive Firmness (NDF) Testing Unit for Fruit", *Transactions of ASAE*, 762–767 (1977).

Wan et al., "Engineering Definition of Firmness", *ASAE*, 1–19 (1991).

Finney, E. E., Jr., "Vibration Techniques For Testing Fruit Firmness," *J. Text. Stud.* 3:263–283 (1972).

*Primary Examiner*—Hezron E. Williams
*Assistant Examiner*—J. David Wiggins
*Attorney, Agent, or Firm*—Needle & Rosenberg

[57] ABSTRACT

A firmness measuring device for non-destructive testing of objects with rough surfaces (such as fruit) is disclosed. The device comprises the following components: a means to generate an impulsive jet of a fluid (such as air) aimed at the surface of the object under test; a laser to generate a beam of coherent light aimed at the area on the surface of the object under test impacted by the fluid jet; a detector to sense the light reflected off of the surface of the object from the laser beam; an analyzer to determine the amount of deformation of the surface caused by the fluid jet based on the input to the detector; and a controller to coordinate the release of the impulsive jet with the analyzer.

35 Claims, 2 Drawing Sheets

NON-DESTRUCTIVE FIRMNESS MEASURING DEVICE

This invention was funded in part by United States Department of Agriculture grant No. GE 001437. The government may have certain fights in the invention.

BACKGROUND OF THE INVENTION

1. Field of the Invention

The present invention relates to a device and a means for determining the firmness of objects, and more particularly to a device and means for non-destructively measuring the firmness of objects using a fluid jet and a light beam specifically for determining the firmness of food products.

2. Description of Prior Art

Firmness, i.e., resistance to deformation, is a key factor in determining the quality of food products. Consumers consider firmness as a predictor of the storing ability and eating quality of fresh fruits and vegetables. Food buyers use firmness when selecting which lot to purchase. Firmness is also a key factor for growers in deciding on harvest dates and in sorting products at packing houses.

One of the primary functions of a fresh fruit and vegetable packing house is to convert a highly variable incoming flow of a product into packages containing products with uniform quality. Many products continue to ripen after harvest, therefore the items packed must be firmer than desired by the end user. Thus, a critical operation at packing houses is to remove riper items which are often the highest quality and more valuable for regional markets but would become soft and cause wholesale buyers to reject the entire shipment when delivered to distant markets. Soft fruit was also the most frequently reported physiological disorder recorded on USDA inspection forms for plum, peach, and nectarine shipments to the New York market between 1972 and 1985, where 40% of the shipments inspected were rejected for being too soft, Ceponis, Cappellini, Wells, and Lighther, "Disorders in plum, peach, and nectarine shipments to the New York market, 1972-1985," Plant Disease 71(10) 947-952 (1987).

Unacceptable variations in firmness frequently occur during food production, manufacturing processes, and product storage. A common approach for minimizing variability and for marketing products with uniform firmness is to separate items into groups with similar firmness levels.

Presently, manual separation is the only practical method available to packing houses for firmness sorting. The sorting task is labor intensive, monotonous, and inaccurate. Consequently, there is a strong need for development of a mechanical device to separate objects based on firmness.

There are several methods of measuring firmness. One method measures firmness by destroying the item under test. With this method, one randomly selects samples from a lot and measures them under the assumption that they represent the total-population. The traditional measure of fruit firmness is with a penetrometer described in Magness and Taylor, "An Improved Type of Pressure Tester for Determination of Fruit Maturity," USDA Circular 350 (1925). This device destructively measures the firmness of an object by determining the force necessary to penetrate the object with a probe to a predetermined depth. A more recent method is disclosed in Studman and Yuwana, "Twist Test for Measuring Fruit Firmness," 23 J. Texture Studies 215-227 (1992). This reference presents a firmness measurement method based on the moment necessary to rotate a blade attached to a spindle after it is pushed into the fruit.

A disadvantage of destructive testing is that to achieve higher levels of reliability one must destroy greater numbers of the product, and one cannot measure the firmness of every item going through a packing line. Furthermore, the ability for a sample to predict the condition of the lot is especially weak for fruit because weather and other variables prevent the control of processes which affect firmness. Thus, a lot will have large variations that are only partially reduced by manual sorting.

Destructive tests for firmness continue, largely because suitable sensors are not available for measuring firmness of all items in a lot. Consequently, effort has been expended on several approaches for finding a non-destructive firmness method. Such methods have either required mechanical contact between the product and a solid probe or measurement of a secondary property which is subsequently correlated to firmness.

A non-destructive mechanical contact measurement is described in Mizrach and Ronen, "Mechanical Thumb Sensor for Fruit and Vegetable Sorting," 35(1) Transactions of the ASAE 247-250 (1992). In this reference, a "mechanical thumb" is used to measure force-deformation. With this method, the product is deformed by a pin connected to a pivot arm with a micro-switch. Measurement of firmness by deformation using two steel balls pushed against opposite sides of the fruit has been described in Mehlschau, Chen, Claypool, and Fridley, "A Deformeter for Non-Destructive Maturity Detection of Pears," 24(5) Transactions of the ASAE 1368-1375 (1981). Dawson, "Non-destructive Firmness Testing of Kiwifruit," Programme Information and Abstracts of the Second International Symposium of Kiwifruit, Feb. 18, 1991, Massey University, Palmerston North, New Zealand describes a non-destructive firmness tester for kiwifruit based on the displacement of a small mass pushed against the fruit by a spring. A micro-switch indicates when deformation exceeds the present limits. A single lane firmness sorting machine is described in Delwiche, McDonald, and Bowers, "Determination of Peach Firmness by Analysis of Impact Forces," 30(1) Transactions of the ASAE 249-254 (1987). This machine is used for sorting peaches and pears into hard, firm, and soft categories by analyzing the force from the fruit impacting a plate supported by force transducers. The sorting index used in this reference uses a relationship between the peak force and the time required to reach the peak force.

Measurement of firmness by deformation caused by an applied force is possible because the slope of a force-deformation curve is the modulus of elasticity, or stiffness of the product. A standard is available for "Compression test of food material of convex shape," ASAE S368.1, in ASAE Standards, 39th Edition, Am. Soc. Agr. Engrs., St. Joseph, Mich. (1992). Terms are defined and specifications are given for tests using parallel plates, a single plate, a spherical indenter on a curved surface, and a spherical indenter on a flat surface. A section on calculations provides standardized methods for finding force and deformation on bio-yield and to rupture, point of inflection, modulus of deformability, and stress index. An equation relating impact force to time is provided by Zhang and Brusewitz, "Impact force model related to peach firmness," Trans. of the ASAE 34(2) 2094–2098 (1991). This equation relates to the force-time response of peaches impacting a load platform. Other researches have reported on measurements of quantities such as coefficient of restitution and penetrometer peak voltage (maximum deceleration).

Measurement of secondary properties is described in Perry, "A non-destructive firmness (NDF) testing unit for fruit," Trans. of the ASAE 20(4) 727–767 (1977). The device descried in this reference measures firmness using low-pressure air simultaneously applied to small areas on opposite sides of peaches. A rotating steel drum has been used for separating soft oranges from undamaged ones is described in Bryan, Anderson, and Miller, "Mechanically Assisted Grading of Oranges for Processing," 21(6) Transactions of the ASAE 1226–1231, (1978). Finney, "Mechanical Resonance within Red Delicious Apples and its Relation to Fruit Texture," 13(2) Transactions of the ASAE 177–180 (1970) describes non-destructive techniques based on resonant frequencies to evaluate firmness of apples and peaches. The concept of using resonant modes in a sorting machine is described in Peleg, U.S. Pat. No. 4,884,696. (1990). In addition, blueberries and grapes have been sorted by low frequency vibration, Chen and Sun, "A review of non-destructive methods for quality evaluation and sorting of agricultural products," J. Agric. Engng. Res. 49, 85–98 (1991). Nuclear magnetic resonance data from fruit has also been used, Stroshine, Cho, Wai, Krutz, and Baianu, "Magnetic resonance sensing of fruit firmness and ripeness," ASAE technical paper no. 91-6565, ASAE, St. Joseph, Mich. (1991).

Both the non-destructive contact sensors and the sensors that rely upon secondary characteristics share the common problem that they are mechanically complicated and are too slow for packing house operations. A common difficulty is the need for mechanical contact between, the product and the sensor. Mechanical devices limit the speed of operation (except for vibration) and can limit reliability. Speed is also limited in some of the approaches by the need to completely analyze the signal generated. Secondary methods, such as measuring resonant frequencies to evaluate firmness (which may involve striking the fruit with a hard object) often requires that the impulse location be held constant for repeatability. Moreover, there is a need to correlate the results obtained with force-deformation relationships of the fruit which are important to end users and other buyers.

Several non-contact firmness sensors have been developed in testing human eyes for glaucoma. For example, the tonometers of Stauffer (U.S. Pat. No. 3,181,351) and the apparatus of Motchenbacher (U.S. Pat. No. 3,232,099) deform the eye with puffs of air, illuminate the point of deformation with noncoherent light, and then determine the amount of deformation based on the intensity of the light reflected off of the point of deformation. However, these devices are incapable of measuring the firmness of objects with rough surfaces (e.g. fruits) because the intensity of the light reflected off of the surface is a function of both the amount of deformation and the roughness of the reflecting surface—a highly variable parameter in fruits and many other products. Moreover, tonometers designed for testing human eyes are not suitable for testing objects with widely varying ranges of firmness, e.g., tomatoes and apples; furthermore, they are adapted to test objects of rather uniform size, convexity, and firmness and must be carefully aimed at a specific point (the front of the eyeball) to obtain valid measurements.

There is thus a need for a method and apparatus of testing entire lots of fruit effectively, efficiently and non-destructively. There is further a need to directly measure firmness rather than-secondary properties, and to do so without mechanically contacting the fruit so as,to avoid possible damage thereto. It would also be desirable to have a method and apparatus for testing the; firmness of objects having variable surface properties, such as rough surfaces with variable reflectance.

SUMMARY OF THE INVENTION

It is thus an object of the invention to provide a method of directly testing the firmness of fruit and other objects efficiently.

It is a further object of the invention to provide a non-contact method of testing fruit and other objects for firmness.

It is a still further object of the invention to provide an efficient non-destructive method for testing the firmness of objects, including fruit.

A still further object of the invention is to provide a non-destructive method for testing the firmness of objects having variable surface characteristics.

To accomplish these and other objects, the subject invention non-destructively measures the firmness of food products, and other items (e.g., tennis balls) where firmness is a key indicator of quality, without mechanically contacting the object under test by deforming the surface of the object under test and using a displacement sensor to measure the surface deformation. The measured surface deformation is then correlated to the firmness of the object under test. Several methods may be used to deform the surface. Preferably, deformation is accomplished by impinging an impulsive jet of a fluid (e.g., air) onto the surface, although other methods could be used.

Several measurements may be useful for correlating surface deformation to the firmness of the object. These include, but are not limited to, measuring the distance between a fixed point on the firmness measuring device and the object under test before the impulsive jet impinges the object and comparing that distance to the distance when maximum deformation of the object under test has occurred.

Two other measurements which can be correlated to firmness are the rate at which the surface of the object under test deforms as the impulsive jet is applied to it, and measuring the rate at which the surface of the object under test recovers to its nondeformed state after the impulsive jet has ceased.

The displacement sensor used operates by exposing the object under test to one form of energy (e.g., ultrasound; electro-magnetic radiation, such as visible light; microwave radiation; and x-ray radiation). The displacement sensor can be an off-the-shelf laser displacement sensor, a laser displacement sensor specifically designed for use in the firmness measuring device, or any other displacement measuring device capable of measuring deformations in the objects under test.

The preferred embodiment uses an impulsive jet of air to deform the surface of the object and measures the amount of deformation with a laser displacement sensor (e.g., Keyence LB-11, available from Keyence Corp. of America, Fair Lawn, N.J.). The impulsive jet of air impinges the surface of the object with a fixed, predetermined force. The amount of deformation is determined by measuring the distance from a laser light source to the deformed area of the object and back to a light detector near the laser light source.

The amount of deformation is then correlated to the firmness of the object. Although in some instances this could be done by direct calculation, determining the firmness of a particular class of objects as a function of surface deformation may also be done through empirical testing. After a sample of sufficient size has been tested, a standard table of firmness versus surface deformation can be created. Once this has been accomplished, firmness can then be determined by correlating the amount of surface deformation of the object under test to its firmness, such as by curve-fitting techniques or table-lookup, possibly with interpolation.

Displacement can be directly displayed by the inventive apparatus, which would allow one either to calculate firmness directly or to look up the firmness of the object under test in a table which lists firmness as a function of displacement. Alternately, the displacement signal can be supplied in analog or digital form to a firmness indicating device, suitably calibrated to transform the supplied signal into a display indicating the firmness measurement. Automatic means such as a digital computer can also be used by supplying the displacement signal in a form suitable for input into the computer (e.g., a digital signal). The computer can then automatically perform the calculations necessary to compute firmness and/or degree of ripeness (for fruit, firmness would correlate to the measured firmness in a known way—perhaps determined empirically—for each particular type of fruit) and display it in a suitable fashion or control automatic processing and/or packing equipment.

This device can be employed as a fixed unit for firmness testing in a packing house or a factory. In a packing house it would be used to sort fruits and other food products. It would test the firmness of the fruit, correlate the firmness with the ripeness of the fruit (or some other predetermined quality of the fruit), and then control a means to put the fruit into a preselected location based on its firmness.

It could also be employed as a bench-top tester used in a packing house for process control. In this application it would be used for random sampling of the output of line sorters for quality control and line calibration.

It could also be employed as a portable unit for firmness testing in the field of food products (e.g., as a hand-held device used to determine optimal fruit harvest time) or other products where firmness is an important factor (e.g., tennis balls used in tournament play). As an in-the-field fruit tester, it would test the firmness of fruit while still on the tree to determine if it is of the proper ripeness for harvest.

This device has several advantages over the prior art. These include: the deformation force is distributed over all of the test area of the surface of the object as opposed to only the raised portions of an irregular or "bumpy" test area, as would a mechanical device, thus minimizing the damage to the tissues of the object by distributing the applied pressure over a greater surface area rather than concentrating it at one or a few discrete points corresponding to the bumps. The fluid jet has a relatively short acceleration time compared to a mechanical deformation device with its greater inertia and which is therefore unsuitable for packing house operations requiring multiple tests per second; it can be constructed from relatively inexpensive, commercially available parts; and the aiming, size and tolerance of the components is not critical: repeatable relative measurements are sufficient to provide acceptable quality information.

DETAILED DESCRIPTION OF THE INVENTION

Figure 1:
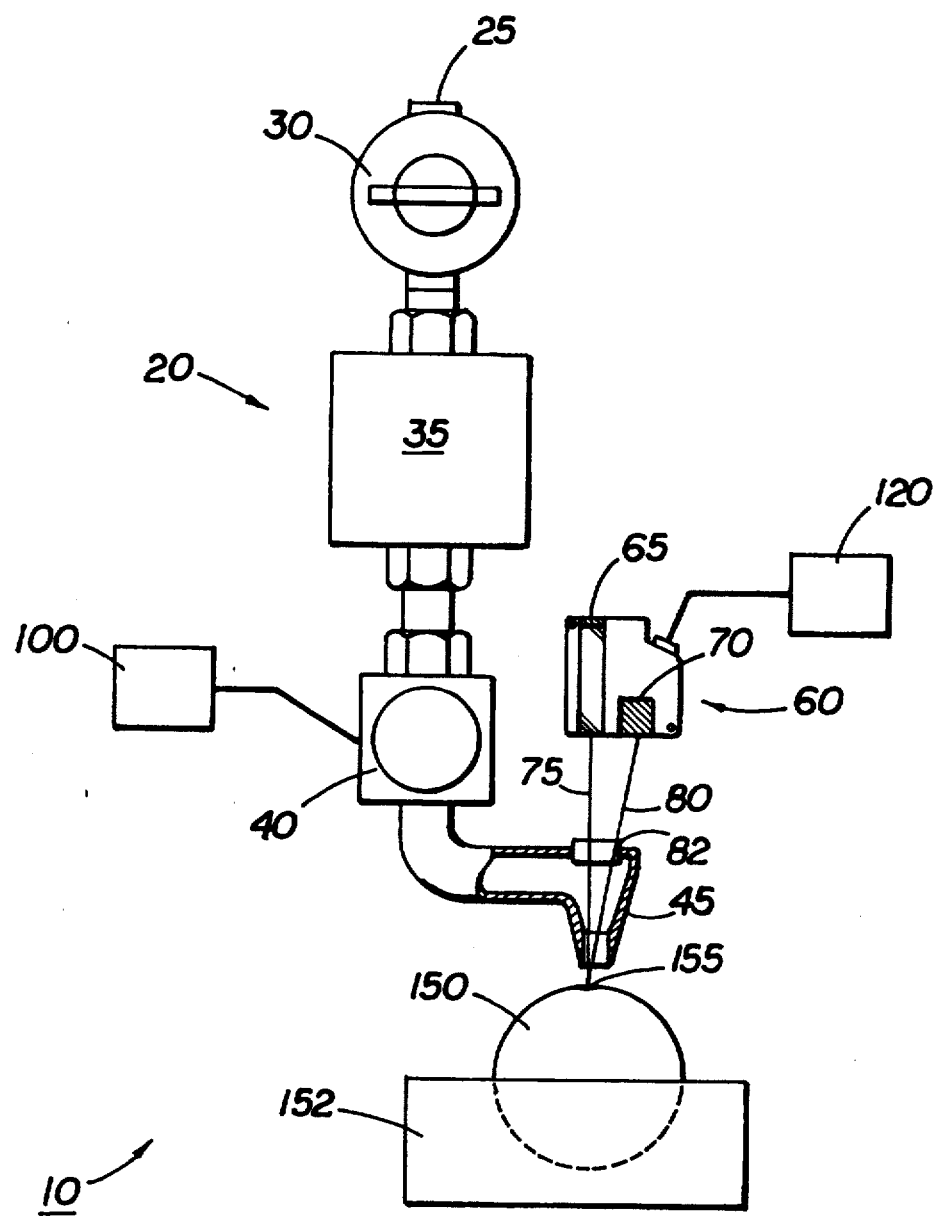
FIG. 1 is a drawing of the preferred embodiment of a firmness sensor in accordance with the invention.

The preferred embodiment, as seen in FIG. 1 at 10, comprises an impulsive air-jet generating unit 20, a surface deformation measuring unit 60, a control unit 100 and an analyzing unit 120. Impulsive jets of air from the air-jet generating unit 20 are aimed at a selected point or area 155 of the surface of the object under test 150. It is an advantage of this invention that variations in surface reflectivity and texture are relatively unimportant in selecting the point or area 155 because the method used for determining deformation is not critically dependent upon the absolute reflectivity of the surface, as will be explained below. The impulsive air jets from the air-jet generating unit 20 deform the surface 155 of the object under test 150 to a greater or lesser extent depending on the following factors: predetermined pressure of the impulsive fluid jet, time duration of the fluid jet, density of the fluid used, and diameter of the fluid jet. The mechanism is one of transfer of the kinetic energy in the air stream to the mass of the object under test.

The air-jet generating unit 20 comprises an air supply 25 which provides air at a pressure not less than the desired pressure of the impulsive air jet to a pressure regulator 30. The pressure regulator 30 discharges at the predetermined pressure of the impulsive air jets to the accumulator 35. The accumulator 35 acts as a reservoir, holding enough air for an impulsive jet of sufficient duration to deform the object under test. It discharges air through the solenoid valve 40, which, under the control of the controller 100, meters the impulsive air jets to the nozzle 45. The nozzle 45 directs the impulsive air jets to the selected area 155 of the object under test 150.

The accumulator 35 must have the capacity to store enough fluid at sufficient pressure such that the impulsive jet from the nozzle 45 is of sufficient duration to deform the object under test 150.

In one embodiment of the air jet generating unit 20, used in the firmness testing of apples, the following specifications were used:

| | | |
|---|---|---|
| supply air pressure | 140 | psia |
| air density in air jet stream | 0.0735 | lbs/cu ft |
| static pressure in air jet stream | 14.7 | psia |
| impact pressure to deform surface | 25.0 | psia |
| mass flow rate | 0.080 | lbs/sec |
| nozzle diameter | ⅛ | in |
| accumulator temperature | 520 | R |
| time duration of jet pulse | 20 | milliseconds |
| max accumulator pressure drop | 5.00 | psi |
| max solenoid valve pressure drop | 5.00 | psi |
| min accumulator volume | 1.60 | cu ft |

-continued

| | |
|---|---|
| connecting pipe diameter | 0.50 in |
| gas flow velocity | 97.65 ft/sec |

The above specifications should not be taken as limitations but merely as an example of empirically determined parameters that were found to be suitable for use in one application.

For most applications in which fruit is being tested, the surface impact pressure will typically be in the range of 0.5 to 60 psia and the length of time that the surface 155 will typically remain deformed will be in the range of 3 to 20 milliseconds. The surface 155 will not be deformed instantaneously, but will require a jet of air sustained for a sufficient period to deform the surface (e.g., in testing apples, it was found to be sufficient to sustain the impulsive jet for 3 to 20 milliseconds).

In one embodiment various items were tested using both a firmer sample and a less firm sample. The following impact pressures were applied to each item to achieve the following measurements:

| Item Tested | Impact Pressure (psia) | Firmness (N) | Deflection (mm) |
|---|---|---|---|
| Kiwifruit | 30.0 | 1.7 | 0.83 |
| | 30.0 | 2.6 | 0.20 |
| Nectarine | 19.0 | 1.0 | 0.30 |
| | 19.0 | 5.4 | 0.08 |
| Orange | 23.0 | 6.8 | 0.24 |
| | 23.0 | 8.2 | 0.18 |
| Plum | 25.0 | 14.2 | 0.70 |
| | 25.0 | 45.5 | 0.13 |
| Potato | 45.0 | 91.0 | 0.14 |
| | 45.0 | 86.0 | 0.19 |
| Hot Dog | 15.5 | 8.6 | 1.16 |
| | 15.5 | 11.0 | 0.70 |

(Where N is relative firmness, in Newtons, as measured by the Magness-Taylor method with an 8mm diameter probe.)

The area deformed by the impulsive jet of fluid is typically about 0.2 inches in diameter, although this area may be adjusted by adjusting the size of the nozzle for any particular application. The distance from the nozzle 45 to the surface of the object under test 155 is not critical as long as the velocity of the impinging air is sufficient to deform the area 155 of the object under test 150. A greater distance from the nozzle to the Surface of the object results in greater attenuation of the velocity of the air jet.

The surface-deformation measuring unit 60 comprises a laser 65 and displacement detector 70. The laser 65 generates an coherent incident light beam 75 aimed at the selected area 155 of the object under test 150. A coherent reflected light beam 80 is reflected from area 155 and returns to the light detector 70. A feature of the invention is that light beam 75 need not be precisely aimed at the center of the area deformed by the impulsive fluid jet, since only relative measurements of deformation are required to evaluate product quality in most instances. It is sufficient that the light beam 75 be aimed sufficiently near the center of the deformed area to obtain repeatable relative measurements of deformation. In addition, although it is preferable that light beam 75 be coherent, it is not necessary that it be either coherent or monochromatic, as long as it can be focused on a sufficiently small spot over the range of deformation distance to be encountered, and that it is accurately detectable by the deformation sensor. Monochromatic coherent light is preferred, however, because the use of such a light source simplifies focusing and detection techniques.

Figure 3:
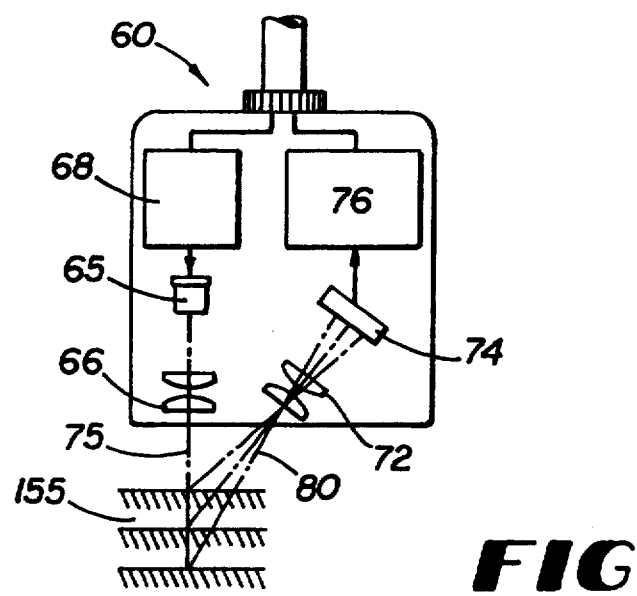
FIG. 3 is a drawing of the laser displacement sensor used in one embodiment of the invention.

Commercially available surface-deformation measuring units suitable for this purpose are available from Keyence Corp. of America, Fair Lawn, N.J. As shown in FIG. 3, the "LB" series displacement sensors (e.g., LB-11 and LB-12) detect targets using triangulation by means of a semiconductor laser 65. The laser 65 is powered by a drive circuit 68. The incident beam of light 75 from the laser 65 is focused on the target by a lens 66. The target surface 155 reflects the incident light to form a reflected beam 80, which is then focused on a position-sensitive detector (PSD) 74 by a lens 72, forming a beam spot. In general, the PSD 74 may comprise a plurality of photodetectors or photocells which are connected to one or more differential amplifiers 76.

Triangulation is then accomplished by determining the difference in the intensity of the part of the beam 80 striking each of the spatially separated sensors in the PSD 74. The difference in intensity results in differing signals from the lihotodetectors or photocells, which are related to the amount of displacement and the diffuseness of the reflection. These differing signals are amplified and processed by the one or more differential amplifiers 76 which supply an analog voltage signal representative of displacement.

As shown in FIG. 1, the incident beam 75 passes through a transparent window 82 in the impulsive air jet generating unit 20 such that it is substantially concentric with the output of the nozzle 45. It is aimed near the center of the area on the surface 155, but can aimed anywhere within one half of the radius of the nozzle 45 from the center of the area 155.

The reflected beam 80 also passes through the window 82 to return to the detector.

The object under test 150 may optionally be held in place by a means 152 for preventing its movement such as a clamp, a hollowed out block, or a dimple on the surface of a conveyor belt. Any other suitable holding means may also be used. This ensures that the object 150 does not move while the firmness measurement is being made. With the proper selection of process parameters the air jet application and displacement sensing can take place in a period short enough that the movement of the fruit on a conveyor line would not affect the result of the test, thus dispensing with the need for a means for preventing movement. Two methods of determining if the fruit being tested is in the proper position to be tested can be employed: a photo sensor (not shown) could detect an object (the fruit) crossing a position on the packing line near to the testing device and trigger a test, or the displacement sensor itself could trigger a test when it detects a minimum in the distance between the sensor and any object under it. More likely, a packing house line would use a combination of the two: the photosensor would detect the presence of fruit and alert the displacement sensor to start looking for a minimum.

Insofar as the operation of the invention is concerned, any fluid which is capable of measurably deforming the surface 155 of the object under test 150 and is transparent to the laser beam 75 (e.g., air, nitrogen, etc.) may be used in the impulsive jet. The jets used to deform the object under test can use specific gasses (e.g. nitrogen or helium for testing objects which might be damaged by being exposed to oxygen; or $SF_6$, which is much heavier and denser than air, for testing objects requiring a more forceful jet in order to be deformed) supplied from a pressurized source, or jets of liquid supplied from a liquid reservoir to deform the object under test. Fluids, such as liquids, that would scatter light from the laser beam 75 could be used if they are aimed at the object under test 150 in such a way that they do not interfere with either the incident laser beton 75 or the reflected laser beam 80.

The surface-deformation measuring unit 60 outputs an analog signal whose voltage represents the distance between the measuring unit 60 and the object under test 150. This signal is fed into the analyzing means 120.

The analyzing means 120 is triggered by the control unit 100 to analyze the analog signal from the measuring unit 60 near the moment of maximum deformation. Conventional peak-detecting circuitry can be used to locate and measure the peak of the analog signal after triggering. An oscilloscope (not shown) can be used to determine the amount of deformation based on peak voltage displayed, the rise time of the voltage signal or the fall time of the voltage signal. Analyzing means 120 may also comprise an analog filtering circuit and meter calibrated to indicate firmness. If desired, the analog signal from measuring unit 60 can be converted to a digital signal by an analog-to-digital converter for further processing. The surface-deformation output may be analyzed and used to control the sorting operations of a packing house. Analysis may typically include the determination of firmness and/or ripeness.

Firmness may be determined by correlating the amount of deformation of the object to its associated firmness. Two other methods to determine firmness are measuring the rate at which the surface of the object under test deforms as the impulsive jet is applied to it, and measuring the rate at which the surface the object under test recovers to its nondeformed state after the impulsive jet has ceased.

Figure 2:
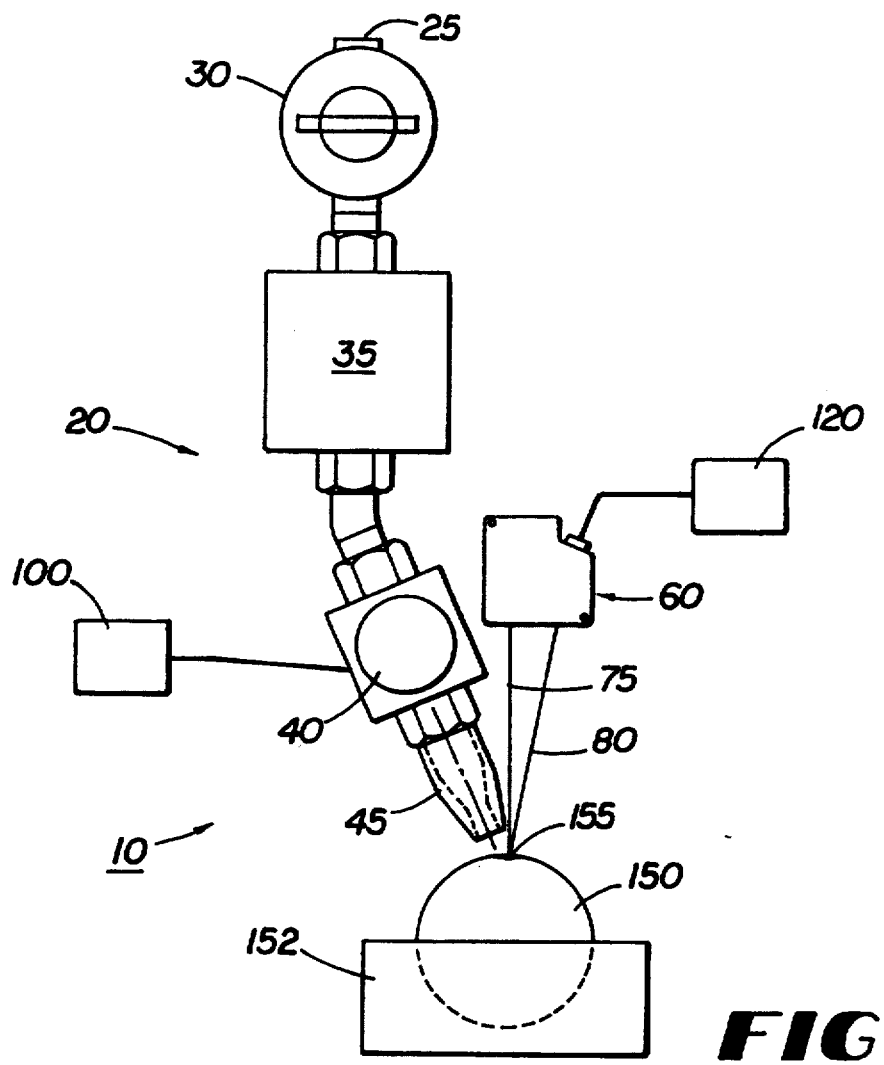
FIG. 2 is an alternative embodiment of a firmness sensor wherein the incident laser beam is not concentric with the center line of the nozzle.

An alternative embodiment is shown in FIG. 2. This embodiment follows the same principles of the embodiment of FIG. 1, except that it does not have the window 82 of FIG. 1, therefore the incident laser beam 75 and the reflected laser beam 80 are not substantially concentric with the nozzle 45. The embodiment of FIG. 2 would be limited, in that care should be taken in this embodiment to avoid interference by the nozzle 45 with the operation of the displacement sensor 60 by blocking the incident laser beam 75. There are two problems associated with this configuration: first, if the laser beam 75 is focused on the center of area 155 of the fruit to be tested 150 prior to the impact of the impulsive jet, then once the surface is deformed, the laser beam 75 will no longer be aimed at the center; and second, if the laser beam is at an angle to the impulsive jet, then, if one draws a right triangle with the axis of the lasher beam 75 being the hypotenuse and the axis of the impulsive jet being the cosine side, the amount of deformation of the fruit 150 will be determined by the change in the position of the surface 155 along the cosine side axis. However, the displacement sensor 60 will measure the change in position along the hypotenuse side, giving an incorrect measurement that will have to be subsequently corrected.

It is possible to direct the light from the laser to the object under test via a fiber optic line passing through the nozzle. This would have the advantage of improving fluid flow, as the laser source could be concentric with the nozzle without having elbows in the fluid line.

The actual amount of deformation of the surface 155 caused by the impulsive air jet is not critical, although it must be within a range that can be sensed and measured by the surface-deformation measuring unit 60 and should be insufficient to damage the object under test. The amount of deformation caused by a jet of any particular duration and force may readily be determined by direct measurement by the surface-deformation measuring unit 60. The force and duration of the jet may be adjusted, if necessary, so that the range of deformations likely to be encountered for the class of objects under test is accommodated within the range that can be measured accurately by the surface-deformation measuring unit 60. There is no necessity that the surface 155 of the object under test 150 be flattened or to reach any particular degree of convexity or concavity. It is only necessary that the range of firmness sought to be measured can be inferred from the measured relative deformation distances and that the object under test not be destroyed by performing the test.

Because it is the relative deformation of the object under test 150 that is measured, it is not necessary to carefully select the portion of the surface 155 under test. Concave, convex, and flat surfaces can all be tested for firmness.

What is claimed is:

1. A firmness measuring device for non-destructive firmness testing of objects, comprising:
    a. means to generate an impulsive jet of a fluid aimed at the surface of the object under test;
    b. means to generate a beam of radiation aimed at the area on the surface of the object under test impacted by said impulsive jet of fluid;
    c. detector means to sense reflected radiation from the surface of the object under test resulting from the reflection of said beam of radiation and to generate a signal representative of the amount of deformation of the object under test;
    d. analyzing means responsive to said signal representative of the amount of deformation of the object under test to determine the firmness of the object under test; and
    e. control means to coordinate the release of said impulsive jet of fluid with the analysis of said signal by said analyzing means.

2. The firmness measuring device of claim 1 wherein the means to generate a jet of a fluid comprises:
    a. a fluid supply means;
    b. a pressure regulating means for receiving fluid from said fluid supply and supplying fluid at a predetermined pressure;
    c. an accumulator means to receive fluid at the predetermined pressure from said pressure regulating means and acts to accumulate a reservoir of fluid;
    d. a valve means to release fluid from said accumulator means in impulsive jets and meter said impulsive jets of fluid; and
    e. a nozzle means to direct said impulsive jets of fluid to the surface of the object under test.

3. The firmness measuring device of claim 1 wherein the fluid is a gas.

4. The firmness measuring device of claim 3 wherein the gas is air.

5. The firmness measuring device of claim 1 wherein the fluid is a liquid.

6. The firmness measuring device of claim 1 wherein the means to generate a beam of radiation is a laser.

7. The firmness measuring device of claim 1 wherein the beam of radiation is visible light.

8. The firmness measuring device of claim 1 wherein the analyzing means determines the firmness of the object by measuring the deformation of the object caused by the impact of the jet of fluid on the surface of the object.

9. The firmness measuring device of claim 1 wherein said means to generate a beam of radiation and said detector means are incorporated in a laser displacement sensor.

10. The firmness measuring device of claim 9 wherein said laser displacement sensor outputs a voltage signal representative of the amount of deformation of the surface of the object under test.

11. A method for measuring the firmness of an object under test having a rough surface, which comprises:
   a. directing an impulsive jet of a fluid having a predetermined force at the surface of the object under test to deform said surface;
   b. directing a beam of coherent electromagnetic radiation at the area on the surface of the object under test impacted by said jet of fluid;
   c. analyzing the electromagnetic radiation from said beam reflected off of said area on the surface of the object under test impacted by said jet of fluid to determine the amount of deformation; and
   d. correlating the amount of deformation of the object under test with the force of said jet of fluid to determine the firmness of the object under test.

12. A device for non-destructively testing the ripeness of food products, comprising:
   a. means to generate an impulsive jet of air aimed at the surface of the food product being tested;
   b. a laser means to generate a beam of coherent light aimed at the surface of the food product under test impacted by said impulsive jet of air;
   c. a detector means to sense reflected light from the surface of the object under test resulting from the reflection of said beam of coherent light and to generate a signal representative of the distance between said detector means and said food product being tested;
   d. an analyzer means responsive to the signal representative of the distance between said detector means and said food product being tested to determine the firmness of the food product under test; and
   e. a controller means to coordinate the release of said impulsive jet of air with the analysis of said signal with the operation of said analyzer.

13. The firmness measuring device of claim 12 wherein said means to generate an impulsive jet of air further comprises:
   a. an air supply means;
   b. a pressure regulating means for receiving air from said air supply and supplying air at a predetermined pressure;
   c. an accumulator means to receive air at the predetermined pressure from said pressure regulating means and acts to accumulate an air reservoir;
   d. a valve means to release air from said accumulator means in impulsive jets and meter said impulsive jets of air; and
   e. a nozzle means to direct said impulsive jets to the surface of the food product under test, 14. A device for non-destructively measuring the ripeness of a food object selected from the group consisting of fruits and vegetables, comprising:
   a. means for non-destructively deforming an area on a surface of a food object under test;
   b. means for measuring the amount of deformation of a surface of a food object under test being deformed by the means for non-destructively deforming an area on a surface of a food object under test; and
   c. means for correlating an amount of deformation measured by the means to measure with ripeness of a food object under test.

15. The device of claim 14 wherein the means for non-destructively deforming a surface of a food object applies pressure to an area of a surface of a food object under test.

16. The device of claim 14 wherein the means for measuring the amount of deformation of a surface of a food object determines the distance between the means for measuring the amount of deformation and a surface of a food object under test deformed by the means for non-destructive deformation.

17. The device of claim 16 wherein the means for measuring comprises a laser displacement sensor.

18. The device of claim 14 wherein the means for non-destructively deforming an area on a surface of a food object impinges an impulsive jet of fluid onto a surface of a food object under test.

19. A method for non-destructively measuring the ripeness of fruit, comprising:
   a. non-destructively deforming an area on the surface of the piece of fruit under test;
   b. measuring the amount of deformation of the surface of the piece of fruit; and
   c. correlating said amount of deformation with the ripeness of the fruit.

20. The method of claim 19 wherein the piece of fruit under test is deformed by impinging an impulsive jet of air onto the surface of the piece of fruit.

21. The method of claim 19 wherein the amount of deformation of the surface of the fruit is determined by measuring the distance between a fixed displacement sensor and the surface of the piece of fruit.

22. A method for non-destructively sorting fruit in a packing house by measuring its firmness, comprising:
   a. non-destructively deforming an area on the surface of the piece of fruit under test;
   b. measuring the amount of deformation of the surface of the piece of fruit;
   c. correlating said amount of deformation with the ripeness of the fruit; and
   d. controlling a means to move pieces of fruit to preselected locations according to ripeness.

23. A method for non-destructively determining the readiness for harvest of fruit while the piece of fruit is still on the tree, comprising:
   a. non-destructively deforming an area on the surface of the piece of fruit under test;
   b. measuring the amount of deformation of the surface of the piece of fruit;
   c. correlating said amount of deformation with the ripeness of the fruit; and
   d. determining whether the fruit is ready to be harvested, based on its ripeness.

24. The device of claim 1 used as a portable firmness sensor for firmness testing of objects in the field.

25. The device of claim 1 used as a bench-top firmness sensor in calibration and quality control of line sorters in a packing house.

26. A device for non-destructively measuring the firmness of objects with rough surfaces, comprising:
(a) means for non-destructively deforming an area on a surface of an object under test;
(b) means for measuring an amount of deformation produced by the means for non-destructively deforming on a surface of an object under test, the means for measuring including a laser displacement sensor for determining a distance between the means to measure and a surface of an object under test being deformed by the means for non-destructively deforming.

27. The device of claim 26 wherein the means for non-destructively deforming applies pressure to a surface of an object under test.

28. The device of claim 26 wherein the means for non-destructively deforming impinges an impulsive jet of fluid onto a surface of an object under test.

29. A method for non-destructively measuring the ripeness of a food object selected from the group consisting of fruits and vegetables, the method comprising:
(a) non-destructively deforming an area on a surface of a food object under test;
(b) measuring the amount of deformation on the deformed area; and
(c) correlating the measured amount of deformation with the ripeness of the food object under test.

30. The method of claim 29 wherein an impulsive jet of air is used to perform the non-destructive deformation.

31. The method of claim 29 wherein the measurement step comprises the measuring of a distance between a fixed displacement sensor and an area of a surface being non-destructively deformed.

32. A method for non-destructively sorting food objects in a packing house according to the ripeness of the food objects, the food objects being selected from the group consisting of fruits and vegetables, the method comprising:
(a) non-destructively deforming an area of a surface of a food object under test;
(b) measuring the amount of deformation of the deformed area;
(c) correlating the measured deformation with a degree of ripeness dependent upon the type of food object under test; and
(d) controlling a means to move tested food objects to preselected locations in accordance with the respective degrees of ripeness determined in the correlating step.

33. A firmness measuring device for non-destructive firmness testing of objects, comprising:
(a) means for generating an impulsive jet of a fluid aimed at a surface of an object under test;
(b) means for generating a beam of radiation aimed at an area on a surface of an object under test impacted by the impulsive jet;
(c) means for sensing reflected radiation from a surface of an object under test resulting from the reflection of said beam of radiation and responsive to the reflected radiation for generating a signal representative of an amount of deformation of an object under test;
(d) means for analyzing the signal representative of an amount of deformation to determine the firmness of an object under test; and
(e) means for coordinating the analysis of the signal representative of an amount of deformation and the release of the impulsive jet.

34. The firmness measuring device of claim 33 wherein the means to generate a jet of fluid comprises:
(a) means for supplying a fluid;
(b) means for receiving the fluid from the means for supplying a fluid and for dispensing the fluid at a predetermined pressure;
(c) means for accumulating a reservoir of fluid from the means for receiving and dispensing the fluid at the predetermined pressure;
(d) means for releasing the fluid in impulsive jets from the means for accumulating a reservoir of fluid and for metering the impulsive jets;
(e) means to direct the impulsive jets of the fluid to a surface of an object under test.

35. The firmness measuring device of claim 34 wherein the means for generating a beam of radiation comprises a laser, and the means for sensing radiation comprises a displacement detector.

* * * * *